United States Patent [19]

Suga

[11] Patent Number: 5,603,330
[45] Date of Patent: Feb. 18, 1997

[54] PULSE COUNTING APPARATUS

[75] Inventor: Fusao Suga, Ome, Japan

[73] Assignee: Casio Computer Co., Ltd., Tokyo, Japan

[21] Appl. No.: 345,132

[22] Filed: Nov. 28, 1994

[30] Foreign Application Priority Data

Dec. 2, 1993 [JP] Japan .................................. 5-303020

[51] Int. Cl.$^6$ .............................. G04B 47/00; A61B 5/04
[52] U.S. Cl. ................................ 128/687; 128/689; 482/8
[58] Field of Search ..................... 128/633, 687, 128/689, 690, 706, 707; 482/3, 7–9, 51, 52, 54, 900, 901; 364/413.01, 413.02, 413.04

[56] References Cited

U.S. PATENT DOCUMENTS

| | | |
|---|---|---|
| 4,105,020 | 8/1978 | Matsuoka et al. . |
| 4,149,526 | 4/1979 | Bargenda et al. . |
| 4,807,639 | 2/1989 | Shimizu et al. . |
| 5,301,154 | 4/1994 | Suga .................................. 128/707 X |
| 5,316,008 | 5/1994 | Suga et al. . |
| 5,323,784 | 6/1994 | Shu .................................... 128/707 |

FOREIGN PATENT DOCUMENTS

0556702A2  8/1993  European Pat. Off. .
2657004   7/1991  France .

OTHER PUBLICATIONS

Philip, J. H., "Improvement in Rate Determining Using a New Method Based on Occurence Times", AAMI 17th Annual Meeting. May 1982.

*Primary Examiner*—Angela D. Sykes
*Assistant Examiner*—Samuel Gilbert
*Attorney, Agent, or Firm*—Frishauf, Holtz, Goodman, Langer & Chick

[57] ABSTRACT

A pulse counting apparatus which has a simple structure and makes few count errors. When the number of pulses at a wrist or the neck of the user counted by means of palpation amounts to 10 and the user stops by using an S1 key the measurement of the pulse counting time period in a timer, it is determined whether the pulse counting time period is 3 seconds or less. If the time period is 3 seconds or less, it is determined that the pulse is miscounted, the value of the timer is cleared and "1" is set in a flag. As a result, the apparatus is switched to a measurement mode. If the time period exceeds 3 seconds, pulses per minute are calculated from the time period and the number of the pulses 10. An exercise intensity corresponding to the pulse is calculated from the pulse and the set age of the user. The pulse and the exercise intensity is displayed in a display.

9 Claims, 8 Drawing Sheets

PULSE COUNTING APPARATUS

BACKGROUND OF THE INVENTION

1. Field of the Invention

The present invention relates to a pulse counting apparatus for obtaining pulse data per unit time by measuring a period of time in which a predetermined number of pulses are generated.

2. Description of the Related Art

Conventionally, in medical facilities, an electrocardiographic signal or pulse generated when the heart contracts is detected by a sensor, and an apparatus for displaying a waveform of the detected signal and an apparatus for calculating the pulses per minute from the signal detected by the sensor, and displaying the pulse have been used. However, since these apparatuses are large and expensive, there has been a demand for a portable pulse counting apparatus, which is inexpensive and which thus allows personal use. In response to the demand, a pulse counting apparatus having a sensor for counting a pulse, applicable to a small apparatus (e.g., a watch), has been put into practice. Such a pulse counting apparatus is disclosed in, for example, U.S. Pat. Nos. 4,807,639 and 5,316,008.

The aforementioned pulse counting apparatus, however, has the following drawback. That is, noise is liable to be generated in a sensor of the apparatus for detecting an electrocardiographic signal or an optical sensor for detecting the pulse. Since noise can result in an inaccurate count, the pulse must be counted repeatedly.

SUMMARY OF THE INVENTION

An object of the present invention is to provide a pulse counting apparatus, which has a simple structure and makes few count errors.

To achieve the above object, a pulse counting apparatus of the present invention comprises:

time measuring means, which starts time measuring in response to a start signal, stops the time measuring within one minute after the time measuring is started, and produces time data;

numerical data storing means for storing predetermined numerical data;

pulse data obtaining means for obtaining pulse data from the predetermined numerical data stored in the numerical data storing means and time data produced by the time measuring means when the time measuring in the time measuring means is stopped; and display means for displaying the pulse data obtained by the pulse data obtaining means.

According to the present invention, a pulse can be detected with a very simple structure, without using a pulse sensor.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

DETAILED DESCRIPTION OF THE PREFERRED EMBODIMENTS

Embodiments of the present invention will be described with reference to the accompanying drawings. In the embodiments, the pulse counting apparatus of the present invention is applied to an electronic watch having a pulse counting function.

Figure 1:
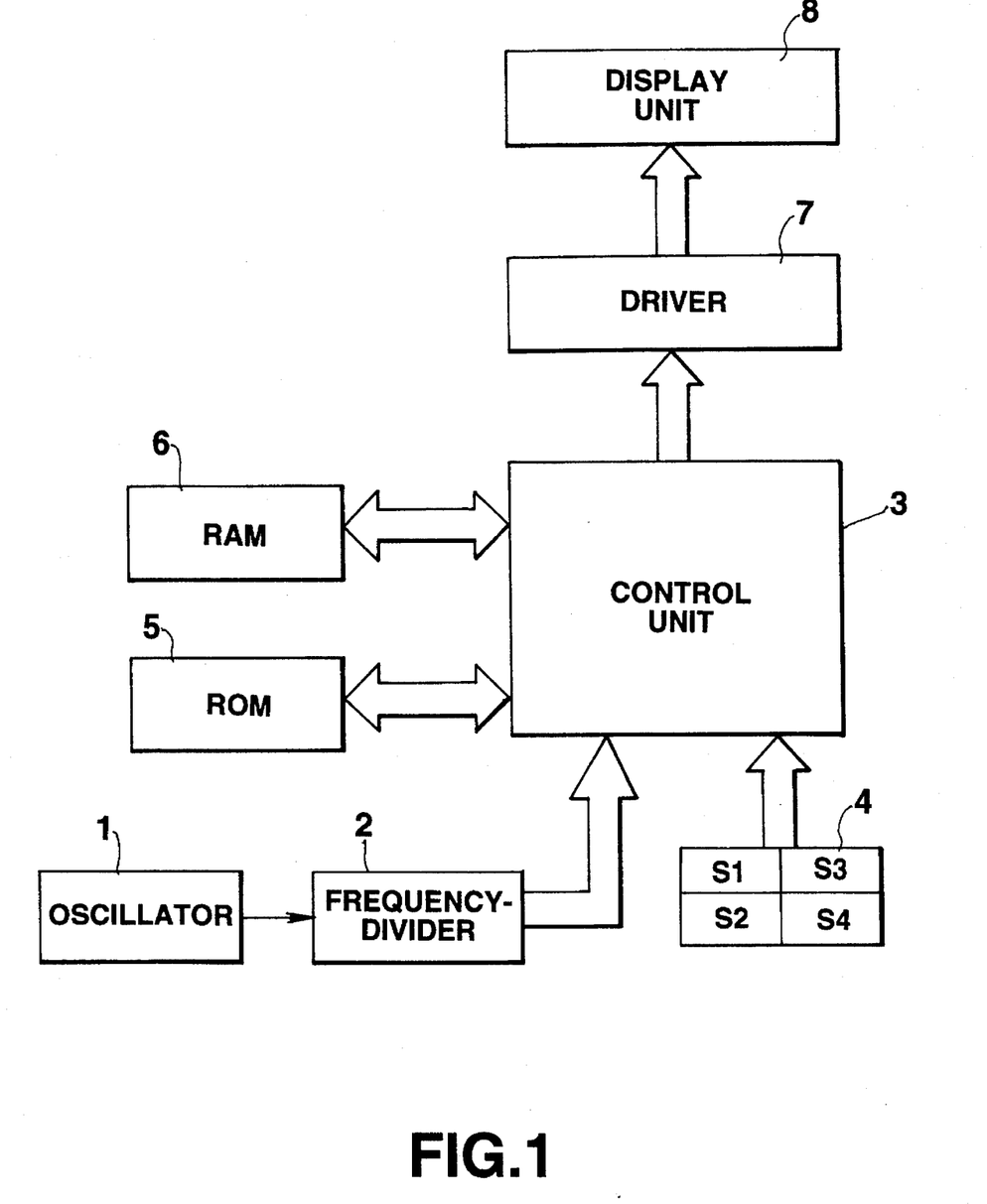
FIG. 1 is a block diagram of a pulse counting apparatus according to the present invention.

FIG. 1 is a diagram showing the structure of the electronic watch having the pulse counting function.

Referring to FIG. 1, an oscillation clock signal of a predetermined frequency generated in an oscillator 1 is divided by a frequency divider 1. A frequency-divided signal is input to a control unit 3. A key input section 4 has an S1 key for switching modes such as a time display mode and a pulse mode, an S2 key for starting and stopping measurement of a pulse counting time, an S3 key for inputting the age of the user and an S4 key for switching the pulse mode to an age setting mode (to be described later) in which an input of the age by means of the S3 key is permitted.

The control unit (central processing unit) 3 executes a key process, a time-counting process, a pulse calculation process (to be described later), and the like, in accordance with a control program stored in a ROM (read only memory) 5, and stores a measured time and a calculation result in a RAM (random access memory) 6. The control unit 3 reads time data or pulse data (to be described later) from the RAM 6, outputs them to a driver 7 and displays them in a display unit 8 such as a liquid crystal display.

Figure 2:
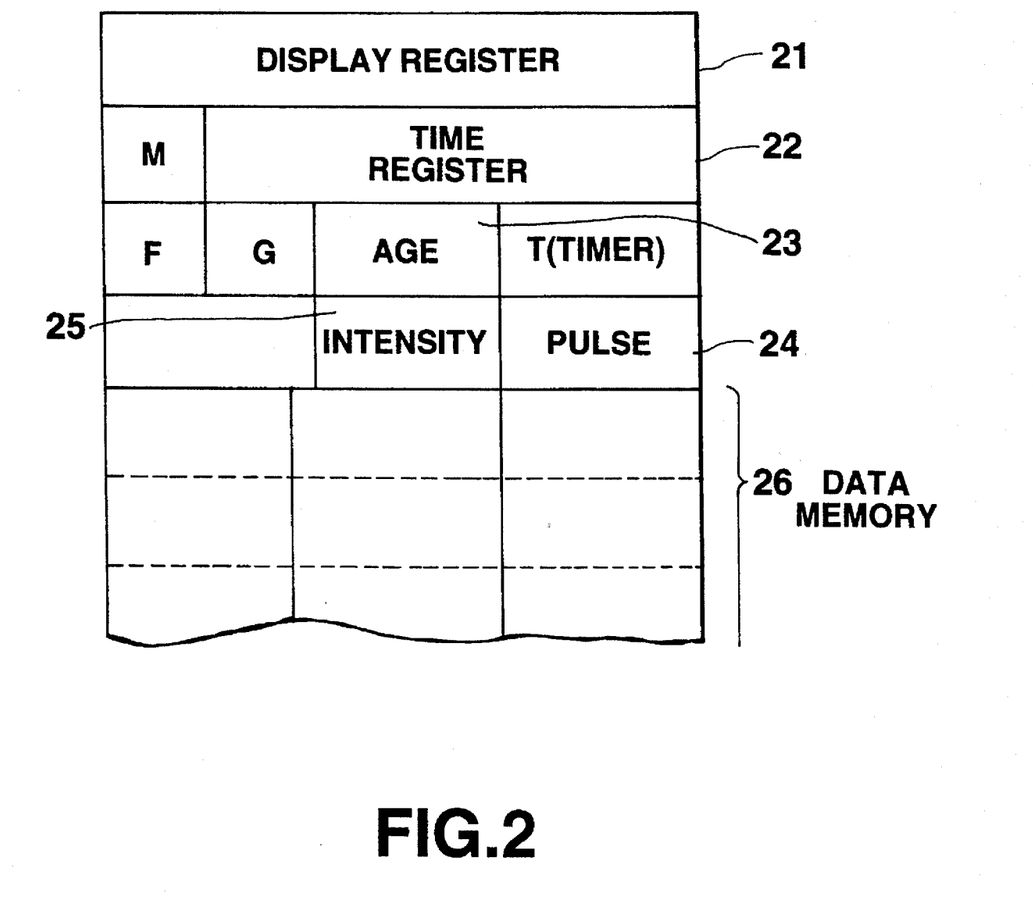
FIG. 2 is a diagram showing the structure of the RAM shown in FIG. 1.

The structure of the RAM 6 will now be described with reference to FIG. 2. A display register 21 stores display data to be displayed in the display unit 8. A time register 22 stores current time data. A mode register M stores numerals corresponding to operation modes: "0" in the time display mode, "1" in the pulse mode and "2" in a recall mode in which pulse data is read from a data memory 26 (to be described later).

A flag F is to distinguish between a pulse count mode and the age setting mode. More specifically, "0" is set to the flag F in the pulse count mode and "1" is set in the age setting mode. As regards a flag G, "1" is set when a pulse counting time is measured and "0" is set in the other situations.

A timer (a time measuring means) T measures a time period in which the user counts a predetermined number (e.g., 10) of pulses by means of palpation. An age register 23 stores age data input by the user. A pulse register 24 stores the number of pulses per minute calculated from an equation based on the period of time measured by the timer T and a predetermined number of pulses. An intensity register 25 stores exercise intensity data calculated by an exercise intensity calculation process (to be described later) based on a maximum number of pulses, depending on the age, and the number of pulses obtained by the calculation (pulse data stored in the pulse register 24).

The exercise intensity data indicates a percentage with respect to the intensity of exercise corresponding to the maximum pulse of the set age. A data memory 26, comprised of a plurality of memory areas, stores the calculated pulse data in order.

An operation of the above embodiment will be described with reference to the flowcharts shown in FIGS. 3 and 4 and the diagram shown in FIG. 5 for explaining the operation modes.

Figure 3:
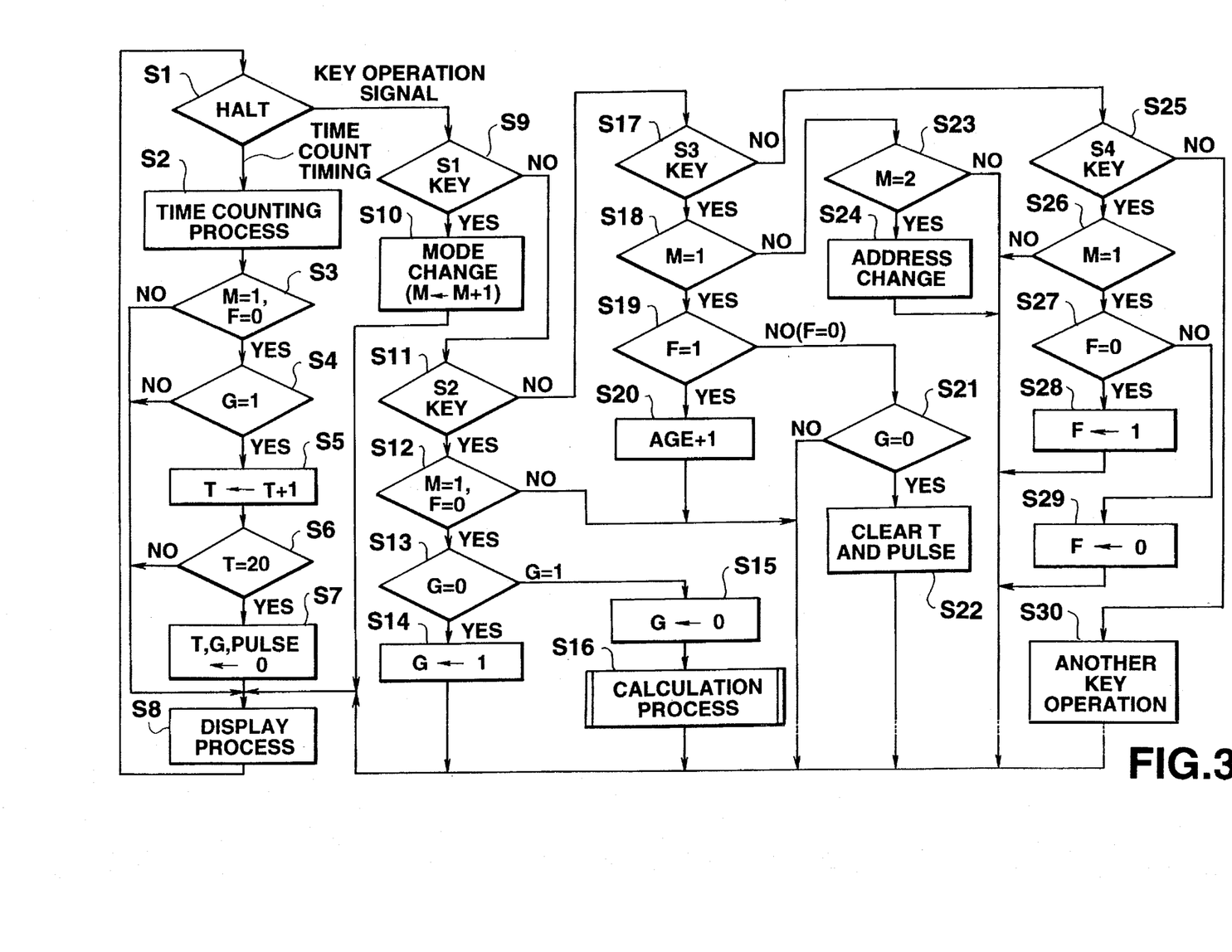
FIG. 3 is a flowchart showing an operation of a pulse counting apparatus according to a first embodiment of the present invention.
Figure 4:
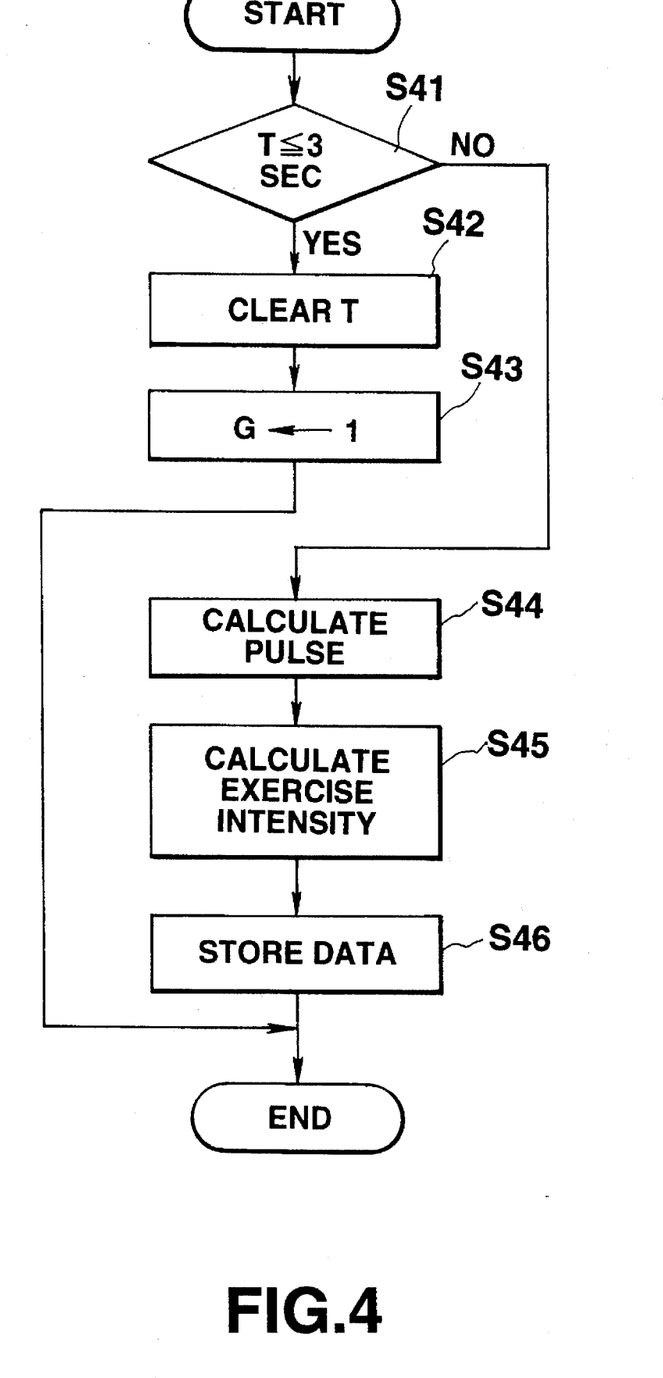
FIG. 4 is a flowchart showing a calculating operation.

When the control unit 3 is in a halt state in a step S1 as shown in FIG. 3, if it detects a timing signal output from the frequency-divider 2, it executes a time counting process of a step S2. If it detects a key operation signal, the flow proceeds to a step S9.

If a timing signal is detected in the step S1, a time counting process of the step S2 is executed. In the time counting process, current time data stored in the time register 22 is updated. Subsequently, in a step S3, it is determined whether the content of the mode register M is "1" (M=1) and the content of the register F is "0" (F=0).

If M≠1 or F≠0 in the step S3, the flow proceeds to a step S8 in which a display process in the corresponding mode is performed. For example, if the operation mode is the time display mode (M=1), the time data stored in the time register 22 is transferred to the display register 21, so that the current date and time are displayed on the display unit 8.

If M=1 and F=0 in the step S3, that is, if the current operation mode is the pulse mode and not the age setting mode, the flow proceeds to a step S4 in which it is determined whether the flag G is "1".

In the step S4, if the flag G is "1", that is, if the pulse counting time is being measured, the flow proceeds to a step S5 in which the value of the timer T for measuring the pulse counting time is incremented by 1. In the next step S6, it is determined whether the value of the timer T amounts to "20", i.e., whether the counting time period amounts to 20 seconds.

In the step S6, if the counting time period amounts to 20 seconds, the values of the timer T and the flag G are cleared in a step S7, so that the operation mode is switched to the initial mode. Thereafter, the display process is executed in a step S8, so as to display the counting time period "0" of the timer T.

The reason why the timer T and the flag G are cleared in the step S7 if the value of the timer T amounts to 20 seconds will be described. In this embodiment, the timer T measured a pulse counting time period in which the number of pulses becomes 10, and calculates pulse per minute from the pulse counting time period. More specifically, assuming that the number of pulses to be counted is X, if a pulse counting time T elapses until the pulses amount to X, the number of pulses per minute Y is obtained by the equation: Y=60X/T. In the apparatus of the embodiment, since the pulse counting time is a period of time which elapses until the pulses amount to x (10), the numerical data of 60×10=600 is prestored in the ROM 5, so that the number of pulses per minute is obtained by the calculation "600/Pulse Counting Time". However, if the pulse counting time of 20 seconds elapses until the pulses amount to 10, the pulses per minute will be 30. Actually, however, the pulses per minute cannot be so low. Therefore, when the value of the timer T becomes 20, the control unit determines that the pulses are miscounted and clears the values of the timer T and the flag G, so that the pulse cannot be calculated from the value of the timer T.

In the step S6, if the value of the timer T is less than 20 seconds, the flow proceeds to the step S8 in which the counting time of the timer T is displayed on the display unit 8.

If a key operation signal is detected in the step S1, the flow proceeds to the step S9, in which it is determined whether the S1 key is operated. If the S1 key is operated, the flow proceeds to a step S10, in which the value of the mode register M is incremented by 1, thereby changing the operation mode. Subsequently, the display process of step S8 is executed, so that a display process in the corresponding mode is performed.

In the step S9, if a key other than the S1 key is operated, the flow proceeds to a step S11, in which it is determined whether the S2 key is operated. If the S2 key is operated, the flow proceeds to a step S12, in which it is determined whether the value of the mode register M is "1" and the value of the flag F is "0".

In the step S12, if M=1 and F=0, the flow proceeds to a step S13, in which it is determined whether the flag G is "0". In the step S13, if the flag G is "0", i.e., if the S2 key is operated in the initial mode of the pulse mode, the flow proceeds to a step S14, in which the flag G is set to "1" and the mode is switched to a pulse count time measurement mode, so as to start the measurement of the pulse counting time in the timer T. Thereafter, the display process of the step S8 is executed to display the pulse counting time in the timer T.

If the flag G is "1" in the step S13, i.e., if the S2 key is operated while the pulse counting time is being measured, the flow proceeds to a step S15, in which the flag G is set to "0" and the current operation mode is switched to a pulse display mode and the measurement of the pulse counting time of the timer T is stopped. At the same time, the calculation in a step S16 is executed.

The calculation process executed in the step S16 will now be described with reference to the flowchart of FIG. 4. First, in a step S41, it is determined whether the value of the timer T, when the measurement is stopped, is 3 seconds or less. If the period of time in which the pulses amount to 10 is 3 seconds or less, the pulses per minute will be 200 or greater. Since, in general, the number of pulses per minute cannot be so great, the control unit determines that the pulses are miscounted by the user and clears the value of the timer T in a step S42. Further, "1" is set to the flag G, so that the operation mode is switched to the measurement mode.

If in the step S41, the value of the timer T exceeds 3 seconds, the pulse is calculated in a step S44, i.e., the calculation "600/Pulse Counting Time" (the period of time measured by the timer T until the pulses amount to 10) is executed so as to obtain the pulses per minute. Further, in a step S45, intensity of exercise is calculated from the age data stored in the age register 23 and the pulse data calculated in the step S44.

There is a relationship between the age of a person and his or her maximum pulse. That is, the maximum pulse of a person of an age is represented by "220-Age". In the aforementioned calculation of the exercise intensity, assuming that the exercise of the intensity "100" results in the maximum pulse, the intensity of the exercise, corresponding to the calculated pulse, is obtained from the ratio of the calculated pulse to the maximum pulse. For example, the maximum pulse of a person of 20 years old is 220−20=200. In this case, if the pulse of the person is 180 when he or she performs an exercise, the intensity of the exercise is (180/200)×100=90%.

When the calculation of the pulse and the exercise intensity has completed, the calculated pulse data is stored in the data memory 26 in a step S46.

Mode switching by means of the S1 key and S2 keys will be described with reference to FIG. 5. In the time display mode in which M=0, when the S1 key is operated, "1" is set to the mode register M, the apparatus is switched to the pulse mode.

Figure 5:
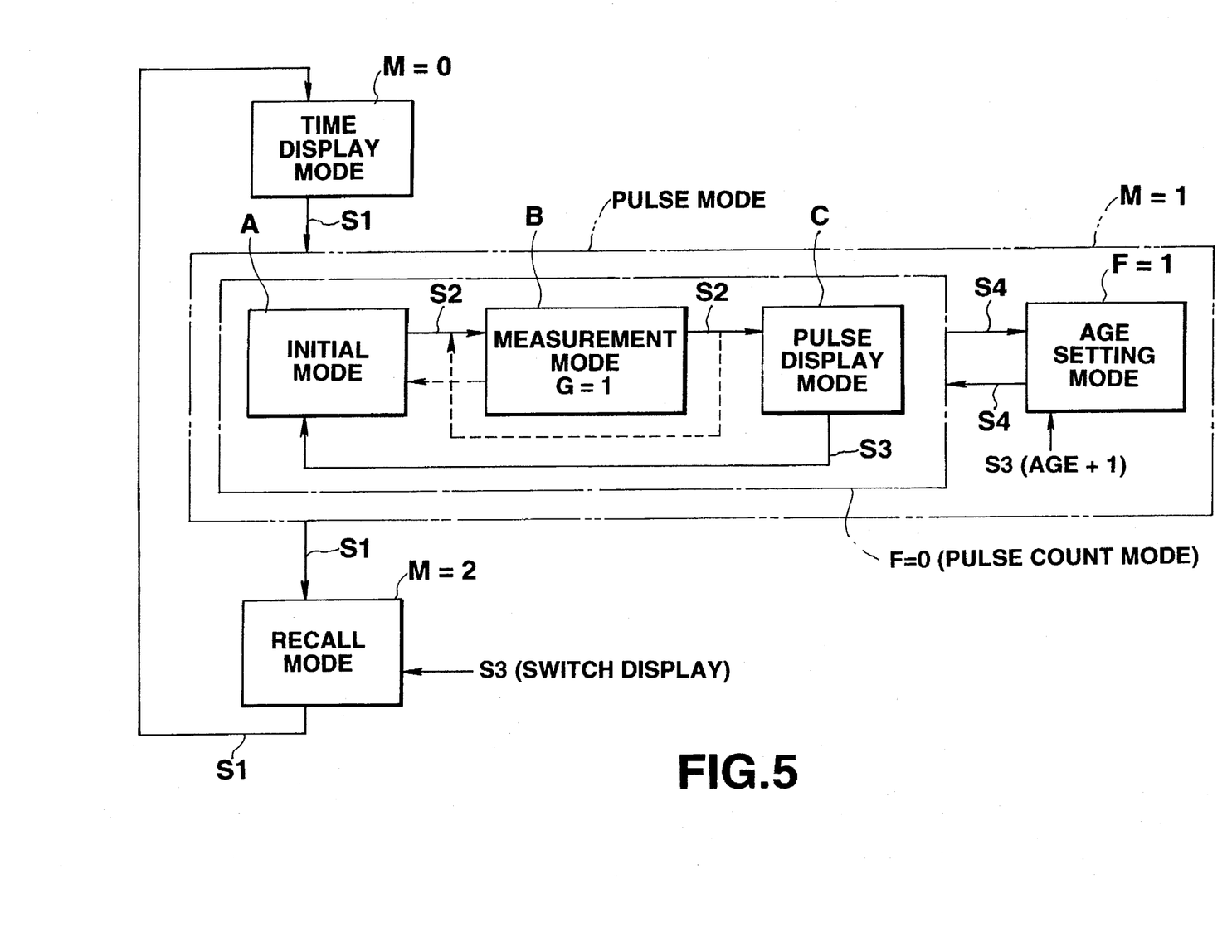
FIG. 5 is a diagram for explaining a mode switching operation.

Immediately after the mode is switched to the pulse mode, "0" is set to the flag G and the apparatus is set in the initial mode as indicated by A in FIG. 5. In this state, when the S2 key is operated, "1" is set to the flag G and the apparatus is set in the measurement mode as indicated by B in FIG. 5, at which time, a time measurement operation of the timer T is started. If the S2 key is operated within 3 seconds of the start of the time measurement operation of the timer T, the measured time is cleared and the measurement operation is performed again. If the S2 key is not operated in 20 seconds, the apparatus is returned to the initial mode. If the S2 key is operated in 3 to 20 seconds after the start of the time measurement operation, "0" is set to the flag G and the apparatus is set in the pulse display mode and the time measurement operation of the timer T is stopped. In the pulse display mode, the pulses per minute and the exercise intensity are calculated from the time measured by the timer T and the pulse 10 measured in the time, and displayed in the display 8.

In the pulse mode in which M=1, when the S1 key is operated, the value of the mode register M is changed to "2", i.e., the apparatus is switched to the recall mode. In the recall mode, the pulse data stored in the data memory 26 can be successively displayed by operating the S3 key.

Figure 6:
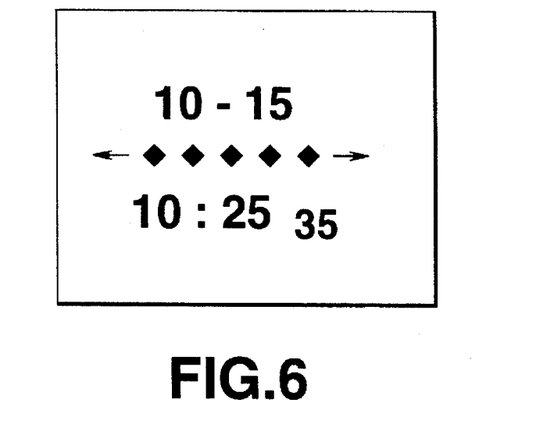
FIG. 6 is a diagram showing a state of the display in a time display mode.
Figure 7:
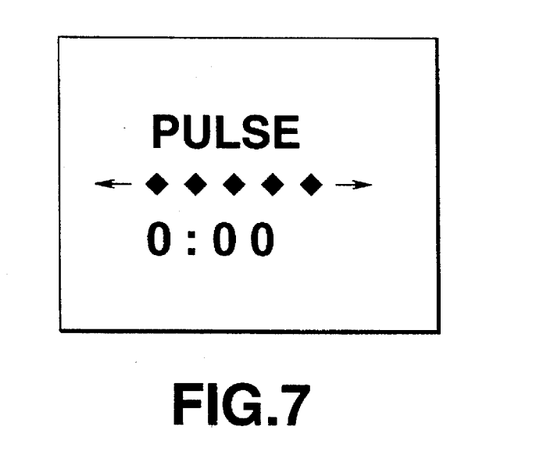
FIG. 7 is a diagram showing a state of the display in an initial mode of a pulse mode.
Figure 8:
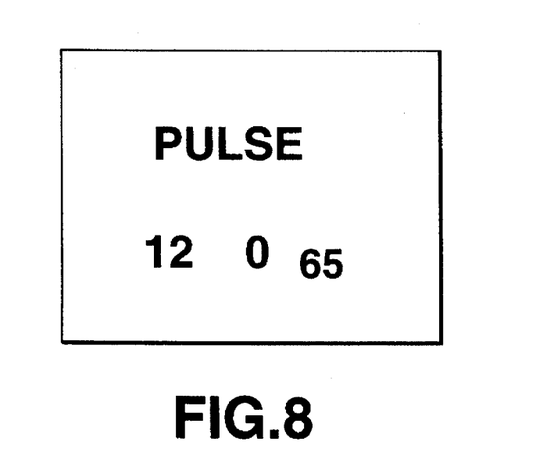
FIG. 8 is a diagram showing a state of the display in a pulse display mode.

FIGS. 6 to 8 show states of the display in the time display mode, the initial mode and the pulse display mode. FIG. 6 shows a state of the display in the time display mode, indicating the current date and time, October 15, 10:25 35". FIG. 7 shows a state of the display in the initial mode, indicating the letters "PULSE" and the initial value ":00" of the timer. FIG. 8 shows a state of the display in the pulse display mode, indicating the pulse per minute "120" and the exercise intensity "65%" calculated from the pulse and the age.

Referring to FIG. 3 again, in the step S11, if the S2 key is not operated, the flow proceeds to a step S17, in which it is detected whether the S3 key is operated. If the S3 key is operated, it is determined whether the value of the mode register M is "1" in a step S18. If the S3 key is operated in the pulse mode (M=1), it is determined whether the flag F is "1" in a step S19.

If "YES" in the step S19, i.e., if the S3 key is operated in the age setting mode in which M=1 and F=1, the flow proceeds to a step S20, in which the value of the age register 23 is incremented by 1.

If the flag F is not "1" in the step S19, i.e., if the S3 key is operated in the pulse mode in which F=0, the flow proceeds to a step S21 in which it is determined whether the flag G is "0". If the flag G is "0" in the step S21 (i.e., if the S3 key is operated in the pulse display mode), the timer T and the pulse register 24 are cleared in a step S22 and the apparatus is returned to the initial mode.

If the value of the mode register M is not "1" in the step S18, the flow proceeds to a step S23 in which it is determined whether the value of the mode register M is "2". If M=2, i.e., if the apparatus is in the recall mode, the read address in the data memory 26 is increased in a step S24. In other words, in the recall mode, the pulse data stored in the data memory 26 can be successively displayed by operating the S3 key. It is possible that the step S24 includes a process of calculating the exercise intensity from the read pulse data and the age data read from the age register 23 and displaying the calculated intensity.

The function of the S3 key will be described with reference to FIG. 5. In the age setting mode (M=1, F=0), each time the S3 key is operated, the value of the age register 23 is incremented by 1. Thus, the age of the user can be set by operating the S3 key in the age setting mode. When the S3 key is operated in the pulse display mode (M=1, F=0, G=0), the timer T and the pulse register 24 are cleared and the apparatus is switched to the initial mode. When the S3 key is operated in the recall mode (M=2), the pulse data stored in the data memory 26 are successively read out.

Referring to FIG. 3 again, if the S3 key is not operated in the step S17, the flow proceeds to a step S25 in which it is determined whether the S4 key is operated. If the S4 key is operated in the step S25, it is determined whether the value of the mode register M is "1" in a step S26. If M=1, it is determined whether the flag F is "0" in a step S27.

If F=0 in the step S27, i.e., if the S4 key is operated in the pulse mode, "1" is set in the flag F in a step S28, thereby switching the apparatus to the age setting mode. If F=1 in the step S27, i.e., the S4 key is operated in the age setting mode, the flow proceeds to a step S29 in which "0" is set to the flag F, thereby switching the apparatus to the pulse mode. If the S4 key is not operated in the step S25, the flow proceeds to a step S30, so that another key operation can be executed.

A mode switching process by means of operating the S4 key will be described with reference to FIG. 5. As shown in FIG. 5, when the S4 key is operated in the pulse mode (M=1, F=0), the apparatus is switched to the age setting mode. In the age setting mode, a desired age can be set by operating the S3 key as described above. When the S4 key is operated in the age setting mode (F=1), "0" is set to the flag F and the apparatus is switched to the initial mode of the pulse mode. In the pulse mode, the pulse counting time period can be measured by operating the S2 key as described above. In this embodiment, as described above, when the period of time, in which the pulses amounts to a predetermined number, is measured, if the measured period of time is too short (shorter than a first reference period of time, e.g., 3 seconds in the embodiment) in a logical sense or too long (longer than a second reference period of time, e.g., 20 seconds in the embodiment), the measured period of time is invalidated. In this way, even if the user miscounts pulses, the miscounted pulse rate is not displayed.

Figure 9:
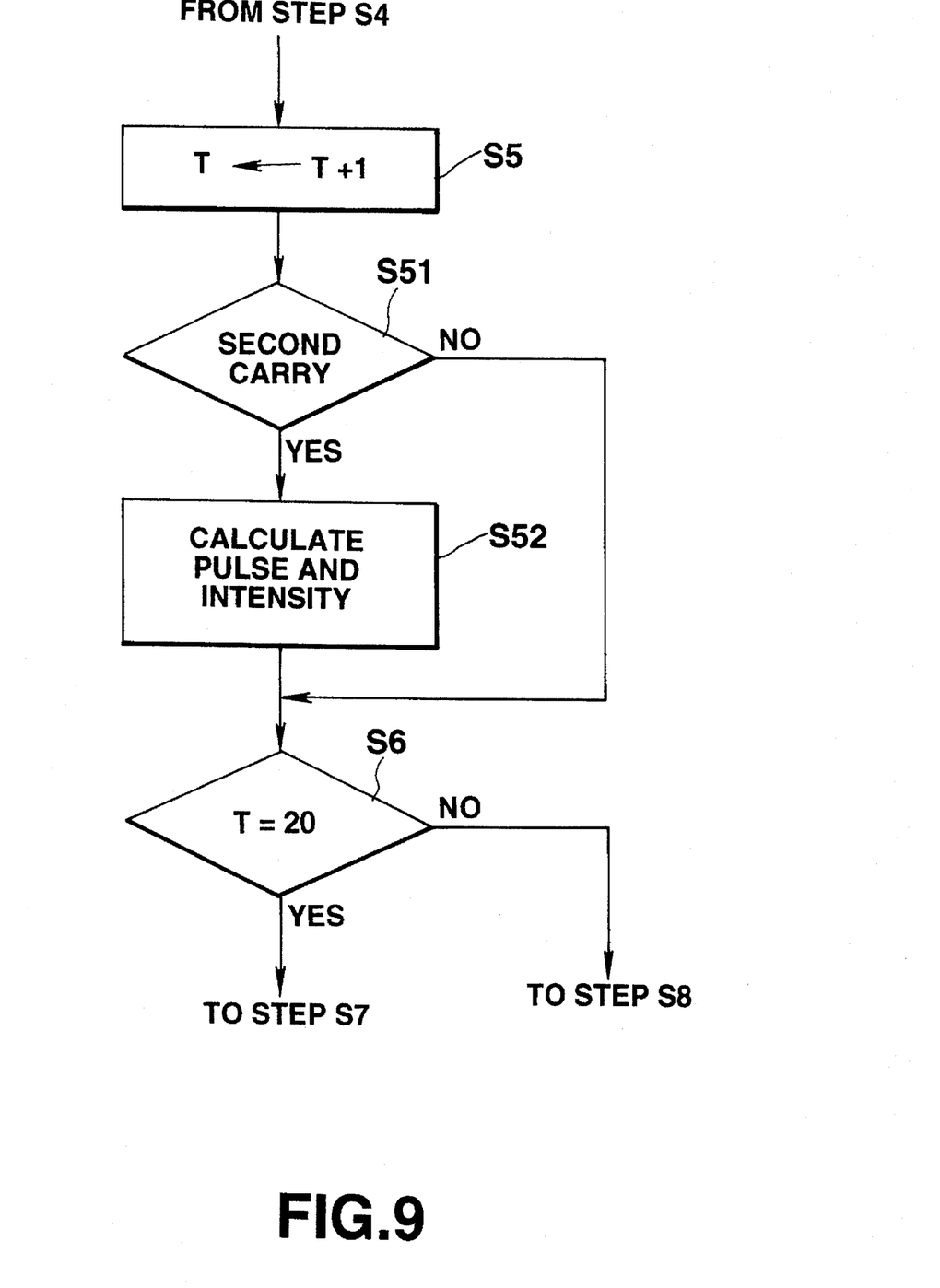
FIG. 9 is a flowchart showing an operation of a pulse counting apparatus according to a second embodiment of the present invention.

A second embodiment of the present invention will now be described with reference to FIGS. 9, 10A and 10B. In an operation of the second embodiment, after the time measurement operation by the timer T starts in the pulse mode, the number of pulses per minute is calculated in every second based on the period of time measured by the timer T and the predetermined number of pulses (e.g., 10 pulses in the embodiment) and the calculated pulse is displayed.

In the following, only portions different from those of the first embodiment shown in FIG. 3 will be described. FIG. 9 is a flowchart showing processes of the second embodiment inserted between the steps S5 and S6 of the flowchart of FIG. 3.

After the timer is incremented by 1 in the step S5, it is determined whether a second carry is generated in a step S51. If a second carry is generated, a calculation of pulse and intensity is executed in a step S52. The calculation is the same as the calculation of pulse in the step S44 and the calculation of intensity in the step S45 shown in FIG. 4. That is, pulses per minute is calculated from the value of the timer T and the number (10) of pulses and the exercise intensity is calculated from the pulses per minute and the age. Thereafter, in the step S6, it is determined whether the timer T counts to 20 seconds. The subsequent steps are the same as those shown in FIG. 3.

Figure 10A:
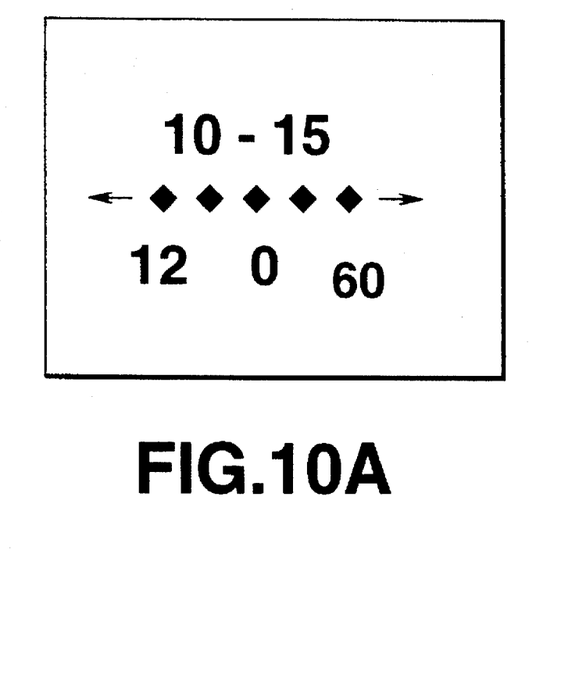
FIGS. 10A and 10B are diagrams showing states of the display in a pulse counting operation of the second embodiment.

FIG. 10A shows a display when 5 seconds have elapsed from the start of the measurement of the pulse counting time. In this case, since the pulse amounts to 10 in 5 seconds, the pulses per minute "120" is displayed. Further, since the user is 20 years old in this case, the exercise intensity is calculated by the equation $(120/200) \times 100 = 60$ and the calculation result "60" % is displayed.

Figure 10B:
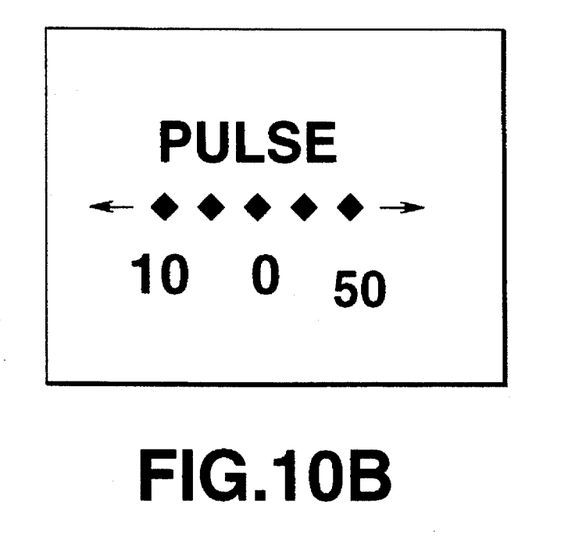

FIG. 10B shows a display when 6 seconds have elapsed from the start of the measurement of the pulse counting time. In this case, since the pulse amounts to 10 in 6 seconds, the pulses per minute "100" is displayed. Further the exercise intensity "50" % is obtained and displayed. In the second embodiment, the pulses per minute is calculated and displayed every second after the start of the measurement of the pulse counting time. Therefore, the number displayed when the user amounts 10 pulses is the pulses per minute of the user. It is thus unnecessary to stop the measurement of the period of time.

In the above embodiments, the pulses per minute is obtained by the calculation "600/Pulse Counting Time". However, the number of pulses to be counted is not limited to 10 but can be 5, 20 or any other number and the calculation can be modified accordingly. Further, it is possible that a table data of pulses per minute corresponding to the pulse counting time is stored in the ROM, so that the data in accordance with the time can be read. In this case, the calculation is not required.

Moreover, the present invention is not limited to the watch as used in the above embodiments but can be applied to any other device having a time measuring function.

As has been described above, the present invention has the following advantages. First, pulses per unit time can be immediately obtained simply by counting the number of pulses at a wrist or the neck of the user by means of palpation and measuring the period of time in which the pulses amount to a predetermined number. Further, if the measured period of time is too short or long, the period is invalidated, so that an incorrect pulse number cannot be displayed. Furthermore, since the intensity of exercise is displayed along with the pulse, the user can see the degree of the exercise.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A pulse counting apparatus comprising:

time measuring means for measuring a period of time in which pulses of a person amount to a predetermined number, and producing time data;

pulse means for obtaining pulse data representing pulses per unit time based on the time data produced by the time measuring means; and time measurement stopping means for automatically stopping measurement of a period of time in the time measuring means, when the time data produced by the time measuring means is at least a predetermined value.

2. The pulse counting apparatus according to claim 1, wherein the pulse means includes calculating means for dividing numerical data of 60 times the predetermined number by the time data, and outputting a calculation result as the pulse data representing the pulses per unit time.

3. The pulse counting apparatus according to claim 2, further comprising:

age data storing means for storing age data; and exercise intensity calculating means for calculating exercise intensity data from the age data stored in the age data storing means and the pulse data obtained by the pulse means.

4. The pulse counting apparatus according to claim 1, further comprising:

age data storing means for storing age data; and exercise intensity calculating means for calculating exercise intensity data from the age data stored in the age data storing means and the pulse data obtained by the pulse means.

5. The pulse counting apparatus according to claim 1, wherein the pulse means comprises:

numerical data storing means for storing predetermined numerical data; and means for obtaining pulse data representing pulses per minute from the predetermined numerical data stored in the numerical data storing means and time data measured by the time measuring means.

6. The pulse counting apparatus according to claim 1, wherein:

the numerical data storing means stores numerical data of 60 times the number of pulses, which should be counted; and the pulse means includes calculating means for dividing the numerical data of 60 times the number of pulses, which should be counted, by the time data and outputting a calculation result as the pulse data representing the pulses per minute.

7. The pulse counting apparatus according to claim 1, further comprising:

first time measurement control means for controlling start and stop of measurement of a period of time in the time measuring means; and second time measurement control means for clearing the time data and automatically restarting measurement of a period of time in the time measuring means, if the measurement of a period of time is stopped by the first time measurement control means when the time data generated by the time measuring means is not greater than a predetermined value.

8. The pulse counting apparatus according to claim 1, further comprising display means for displaying the pulse data per unit time obtained by the pulse means.

9. The pulse counting apparatus according to claim 1, wherein the pulse means obtains the pulse data representing the pulses per minute each time the time data varies second by second.

* * * * *